United States Patent
Ruddy

(10) Patent No.: US 6,807,964 B1
(45) Date of Patent: Oct. 26, 2004

(54) COLD WEATHER BREATHING DEVICE

(76) Inventor: Michael A. Ruddy, 15630 Bueche Rd., Chesaning, MI (US) 48616

( * ) Notice: Subject to any disclaimer, the term of this patent is extended or adjusted under 35 U.S.C. 154(b) by 0 days.

(21) Appl. No.: 10/751,787

(22) Filed: Jan. 5, 2004

(51) Int. Cl.[7] .................................................. F24J 3/00
(52) U.S. Cl. .......................... 128/204.17; 128/201.13; 128/201.29; 128/203.26; 128/911
(58) Field of Search ...................... 128/204.17, 201.13, 128/201.29, 203.26, 911

(56) References Cited

U.S. PATENT DOCUMENTS

| | | | | |
|---|---|---|---|---|
| 4,062,359 A | * | 12/1977 | Geaghan ................ | 128/204.17 |
| 4,150,671 A | | 4/1979 | Tiger | |
| 4,269,183 A | | 5/1981 | Hunt | |
| 4,441,494 A | * | 4/1984 | Montalbano ........... | 128/204.17 |
| 4,461,292 A | * | 7/1984 | Montalbano ........... | 128/204.17 |
| 4,492,228 A | * | 1/1985 | Makovic ................ | 128/207.17 |
| 4,503,850 A | * | 3/1985 | Pasternak .............. | 128/201.25 |
| 4,793,343 A | | 12/1988 | Cummins, Jr. et al. | |
| 5,029,572 A | * | 7/1991 | LeBlanc .................... | 126/204 |
| 5,063,923 A | * | 11/1991 | Peroni .................... | 128/201.13 |
| 5,265,592 A | * | 11/1993 | Beaussant ............. | 128/201.24 |
| 5,490,501 A | * | 2/1996 | Crowley ................ | 128/204.17 |
| 5,501,212 A | * | 3/1996 | Psaros ................... | 128/205.12 |
| 6,330,883 B1 | * | 12/2001 | Berger ................... | 128/201.13 |

* cited by examiner

Primary Examiner—Henry Bennett
Assistant Examiner—Nihir Patel
(74) Attorney, Agent, or Firm—McKellar Stevens, PLLC; Timothy S. Stevens

(57) ABSTRACT

A cold weather breathing device and method. Exhaled air warmed by the lungs of a user is flowed into contact with a heat exchange medium to heat the heat exchange medium. The heat exchange medium is positioned in a hollow body adjacent the chest and under cold weather outer clothing of the user. Upon inhaling, cold outside air is contacted with the heat exchange medium so that the inhaled air is heated by the heat exchange medium.

12 Claims, 5 Drawing Sheets

US 6,807,964 B1

COLD WEATHER BREATHING DEVICE

BACKGROUND

The instant invention relates to breathing devices for use in cold weather and more particularly to such devices that employ a heat exchanger to transfer heat from exhaled air to inhaled air.

Cold weather breathing devices for use by persons are known. For example, U.S. Pat. No. 4,062,359 to Geaghan disclosed a device employing a face mask having an exit valve with a flexible/porous tube connected to the face mask so that the tube could be positioned adjacent the chest of the user under the user's outer clothing. Air, warmed and humidified by the body of the user, was breathed into the tube, to the mask and then into the lungs of the user. When the user exhaled, the exhaled air was vented from the face mask by way of the exit valve.

U.S. Pat. No. 4,150,671 to Tiger disclosed a device employing a face mask having a heat exchanger positioned therein so that air breathed into the face mask was warmed by previously exhaled air. U.S. Pat. No. 5,063,923 to Peroni disclosed a device employing a mouthpiece connected to a tube, the tube leading to a collecting vessel for the admission of fresh air and air heated by the body, the collecting vessel to be positioned adjacent the chest of the user under the user's outer clothing.

U.S. Pat. No. 4,461,292 to Montalbano disclosed a device employing a mouthpiece connected to a conduit system connected to a chamber positioned adjacent the chest of the user, the conduit having an exit valve so that body heated air was inhaled from the chamber and then exhaled through the exit valve. U.S. Pat. No. 4,269,183 disclosed a device employing a face mask connected to a heat exchanger positioned at the side of the head of the user so that inhaled air was heated by the heat of the exhaled air.

Despite the many and continued advances made in the art of cold weather breathing devices, such devices that employ a face mask are relatively uncomfortable and tend to inhibit the ability of the user to communicate with other persons by voice. Cold weather breathing devices that employ a mouthpiece are more comfortable and the mouthpiece can be temporarily removed for voice communication with other persons. Cold weather breathing devices that exhale air directly to the atmosphere waste the heat of the exhaled air. Cold weather breathing devices that heat inhaled air by heat from exhaled air recover the heat of the exhaled air but position the heat exchanger in a face mask or at the side of the head. It would be an advance in the art of cold weather breathing devices if a device were discovered that was more comfortable to use and positioned a heat exchanger for heating the inhaled air by heat from exhaled air in a better location.

SUMMARY OF THE INVENTION

The instant invention is a cold weather breathing device employing a mouthpiece connected to a flexible conduit that is connected to a heat exchanger so that inhaled air is heated by exhaled air. The heat exchanger is positioned adjacent the chest under the outer clothing of the user of the device.

More specifically, the instant invention is a cold weather breathing device, comprising four elements. The first element is a mouthpiece to be held in the mouth of a user of the device. The second element is a hollow body defined by the walls of the body, the body having a mouth thereinto, the body having an opening therefrom, the body being perforated with an aperture. The third element is a heat exchange conduit having a first end and a second end, the first end of the heat exchange conduit being positioned within the hollow body by way of the aperture, the second end of the heat exchange conduit being positioned outside of the wall of the hollow body, the wall of the hollow body being sealed to the heat exchange conduit at the aperture of the body. The fourth element is a flexible conduit having a first end and a second end, the first end of the flexible conduit being connected to the mouthpiece, the second end of the flexible conduit being connected to the mouth of the hollow body. Air breathed out of the lungs of a user through the mouthpiece flows through the flexible conduit, into the hollow body and then out the opening therefrom thereby heating the portion of the heat exchange conduit positioned within the hollow body. Air that is then breathed into the second end of the heat exchange conduit flows into the hollow body heated by the heated portion of the heat exchange conduit positioned within the hollow body, through the flexible conduit, through the mouthpiece and then into the lungs of the user.

In another embodiment, the instant invention is a method for breathing more comfortably in cold weather, comprising the steps of: (a) exhaling air warmed by the lungs into contact with a heat exchange medium to heat the heat exchange medium, the heat exchange medium being positioned adjacent the chest and under cold weather outer clothing; (b) inhaling air from contact with the heat exchange medium so that the inhaled air is heated by the heat exchange medium.

DETAILED DESCRIPTION OF THE INVENTION

Figure 1:
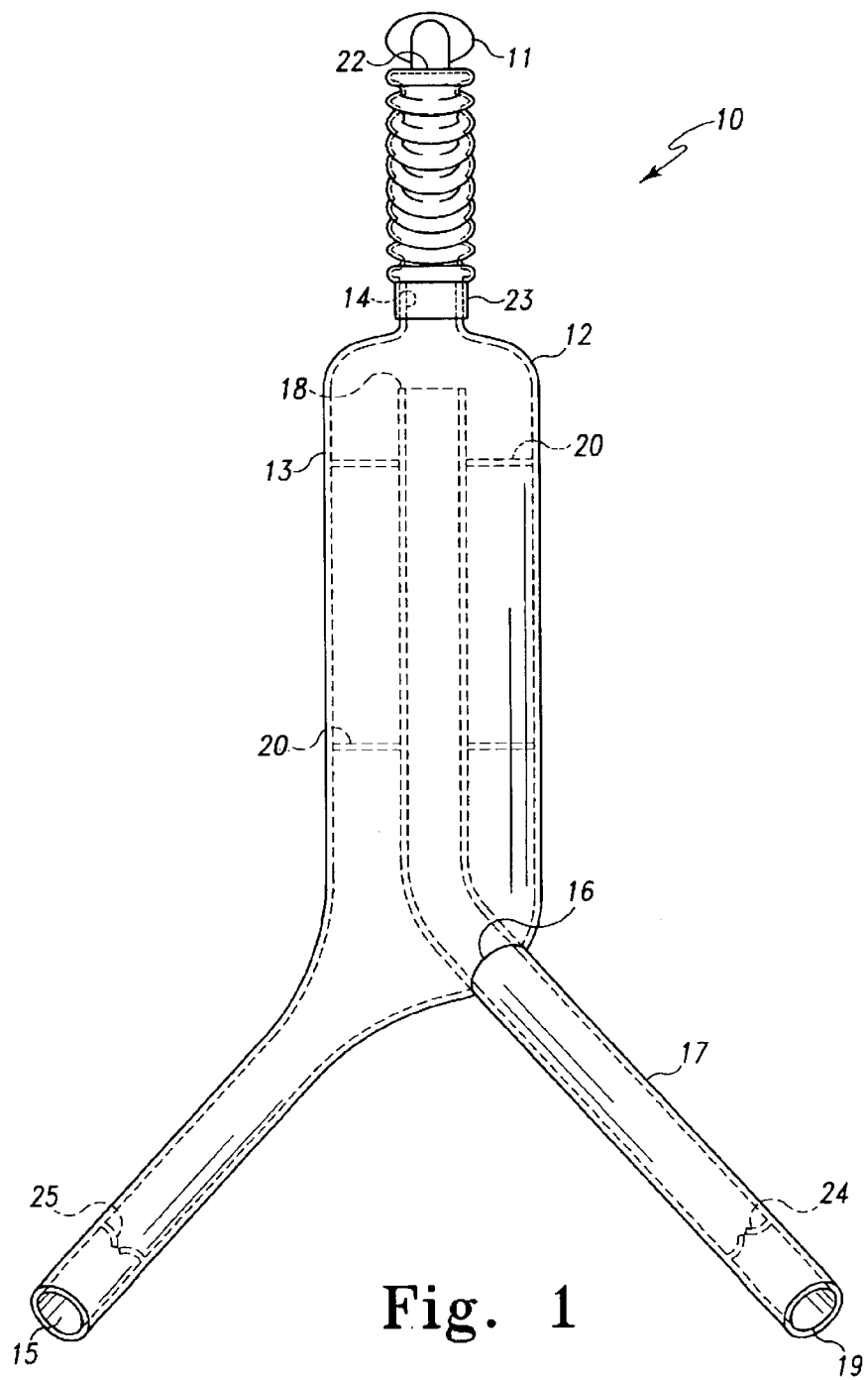
FIG. 1 is a front view of a device according to the teachings of instant invention showing a flexible conduit connected at one end to a mouthpiece and at the other end to a hollow body.
Figure 2:
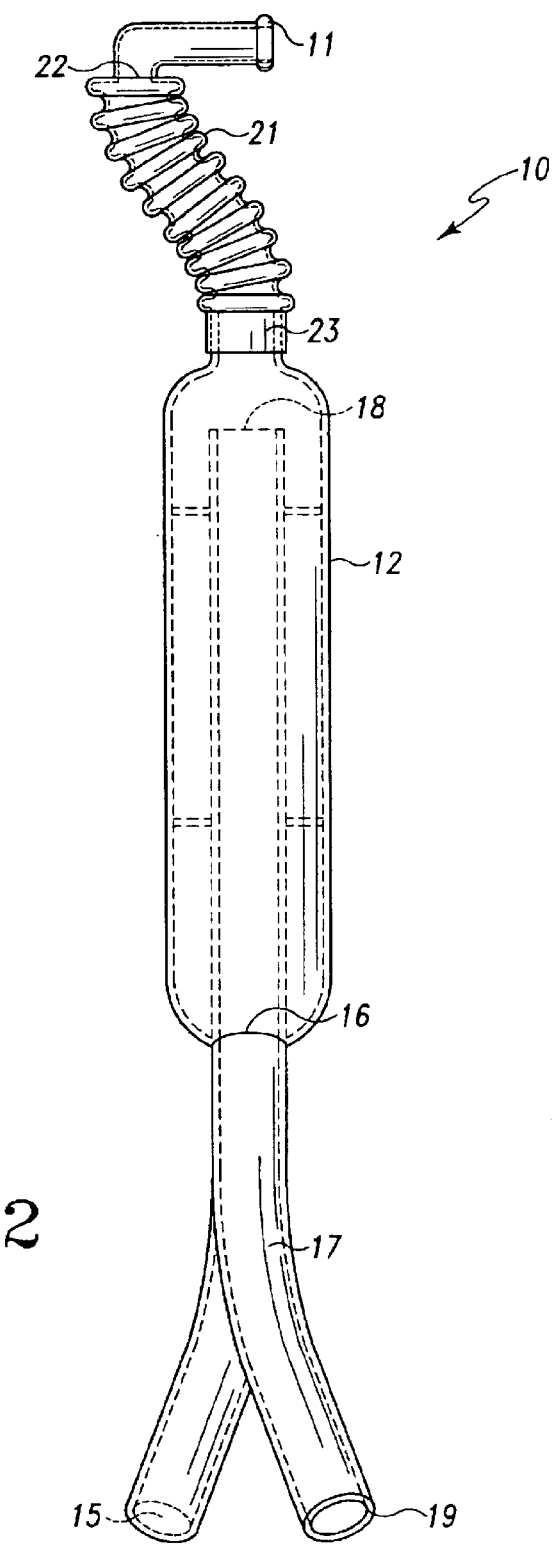
FIG. 2 is a side view of the device shown in FIG. 1.

Referring now to FIGS. 1 and 2, therein is shown a front view and side view, respectively, of a breathing device 10 according to the teachings of the instant invention. The device 10 has a mouthpiece 11 to be held in the mouth of a user of the device and a hollow body 12 defined by the walls 13 of the body, the body 12 having a mouth 14 thereinto and an opening 15 therefrom. The body 12 is perforated with an aperture 16. The device also includes a heat exchange conduit 17 having a first end and a second end. The first end 18 of the heat exchange conduit is positioned within the hollow body 12 by way of the aperture 16. The second end of the heat exchange conduit 19 is positioned outside of the hollow body 12. The wall 13 of the hollow body 12 is sealed to the heat exchange conduit 17 at the aperture 16 of the body 12. Perforated spacers 20 are used to position the heat exchange conduit 17 in the hollow body 12. The design of the mouthpiece 11 is important for the comfort of the user of the device 10. The mouthpiece should be designed, with regard, for example, to thickness and size, for maximum comfort of the user. Most preferably, several different sizes and types of mouthpiece are available to the user so that the most appropriate type can be selected.

Preferably, the inside diameter of the mouth 14 is larger than the outside diameter of the heat exchange conduit 17 so that during construction of the device 10, the second end 19 of the heat exchange conduit 17 can be inserted through the mouth 14, through the perforated spacers 20 and then through the aperture 16. Preferably, the body 12 is made of plastic and molded in two halves that are then joined together. Preferably, the body 12, the spacers 20 and the heat exchange conduit 17 are constructed of plasticized polyvinyl chloride. However, of course, the heat exchange conduit 17 can be made of other materials such as corrugated copper tubing. Preferably, the outside diameter of the heat exchange conduit 17 is slightly larger than the inside diameter of the aperture 16 so that the heat exchange conduit 17 is sealed to the aperture 16 by an interference fit. Alternatively, the heat exchange conduit 17 can be molded integrally with the body 12. Preferably, the mouthpiece 11 is disposable and made of, injection molded polyethylene. The body 12 can be constructed of plastic film, such as polyethylene film.

The device 10 also includes a flexible conduit 21 having a first end 22 and a second end 23. Preferably, the flexible conduit 21 is made of rubber. The first end 22 of the flexible conduit 21 is connected to the mouthpiece 11. The second end of the flexible conduit 21 is connected to the mouth 14 of the hollow body 12 so that air breathed out of the lungs of a user through the mouthpiece 11 flows through the flexible conduit 21, into the hollow body 12 and then out the opening 15 therefrom thereby heating the portion of the heat exchange conduit positioned within the hollow body and so that air then breathed into the second end 19 of the heat exchange conduit 17 flows into the hollow body heated by the heated portion of the heat exchange conduit positioned within the hollow body 12 and then flows through the flexible conduit 21, through the mouthpiece 11 and into the lungs of the user. Preferably, at least one half of the heat of the exhaled air is transferred to the portion of the heat exchange conduit 17 positioned within the hollow body 12. More preferably, at least two thirds of the heat of the exhaled air is transferred to the portion of the heat exchange conduit 17 positioned within the hollow body 12. Most preferably, at least three quarters of the heat of the exhaled air is transferred to the portion of the heat exchange conduit 17 positioned within the hollow body 12

The efficiency of the device 10 is significantly improved if a first check valve 24 is positioned in and sealed to the heat exchange conduit 17 and if a second check valve 25 is positioned in and sealed to the walls of the body adjacent the opening therefrom to prevent back flow of air through the heat exchange conduit 17 when the user exhales through the device and to prevent backflow of air through the opening 15 of the body 12 when the user inhales air through the device, respectively. Preferably, the first check valve 24 and the second check valve 25 comprise a thin flap of rubber as is well known in the art of breathing devices.

Figure 3:
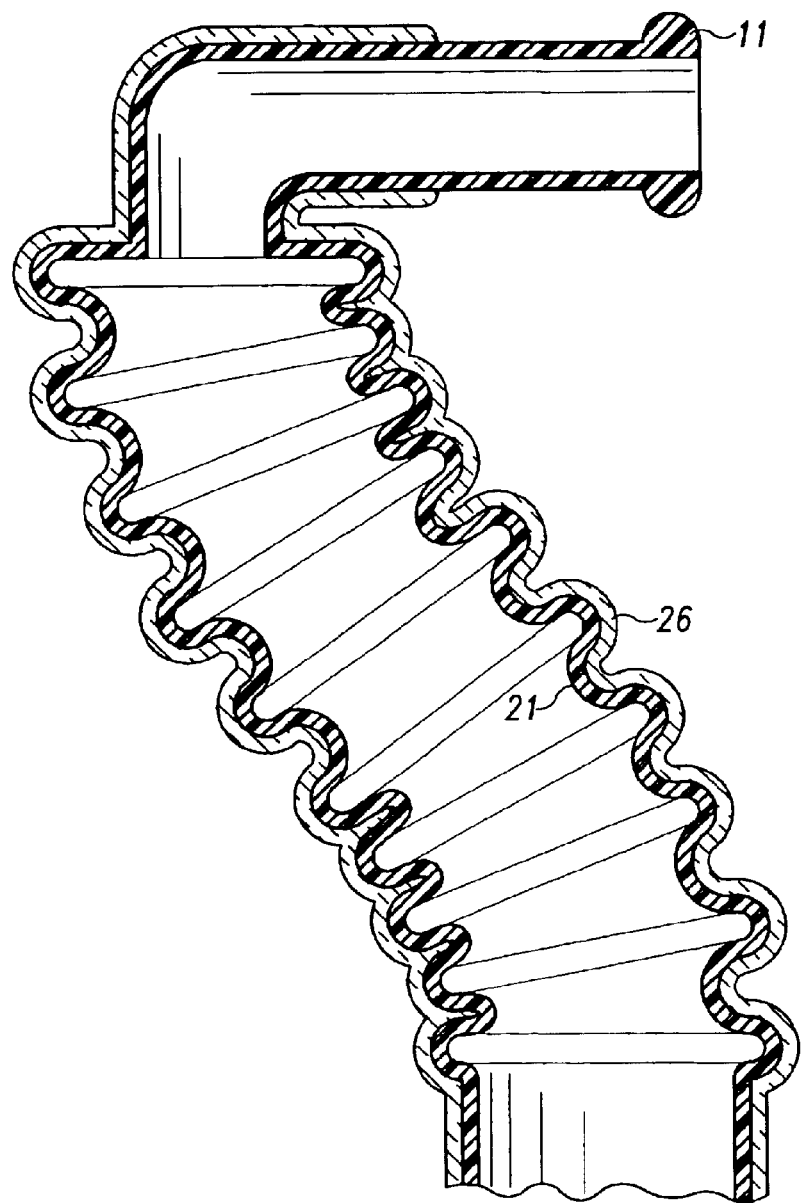
FIG. 3 is a side cross-sectional view of the mouthpiece and upper end of the flexible conduit of FIG. 1 and further showing thermal insulation positioned on and around the flexible conduit.

Referring now to FIG. 3, therein is shown a side cross-sectional view of the mouthpiece 11 and upper end of the flexible conduit 21 of the device 10 of FIG. 1 and further showing thermal insulation 26 positioned on and around the flexible conduit 21. The use of thermal insulation 26 is preferred to conserve the heat of exhaled air and to inhibit condensation of moisture in the flexible conduit 21. The thermal insulation 26 is most preferably a tube of knitted yarn such as knitted wool yarn.

Figure 4:
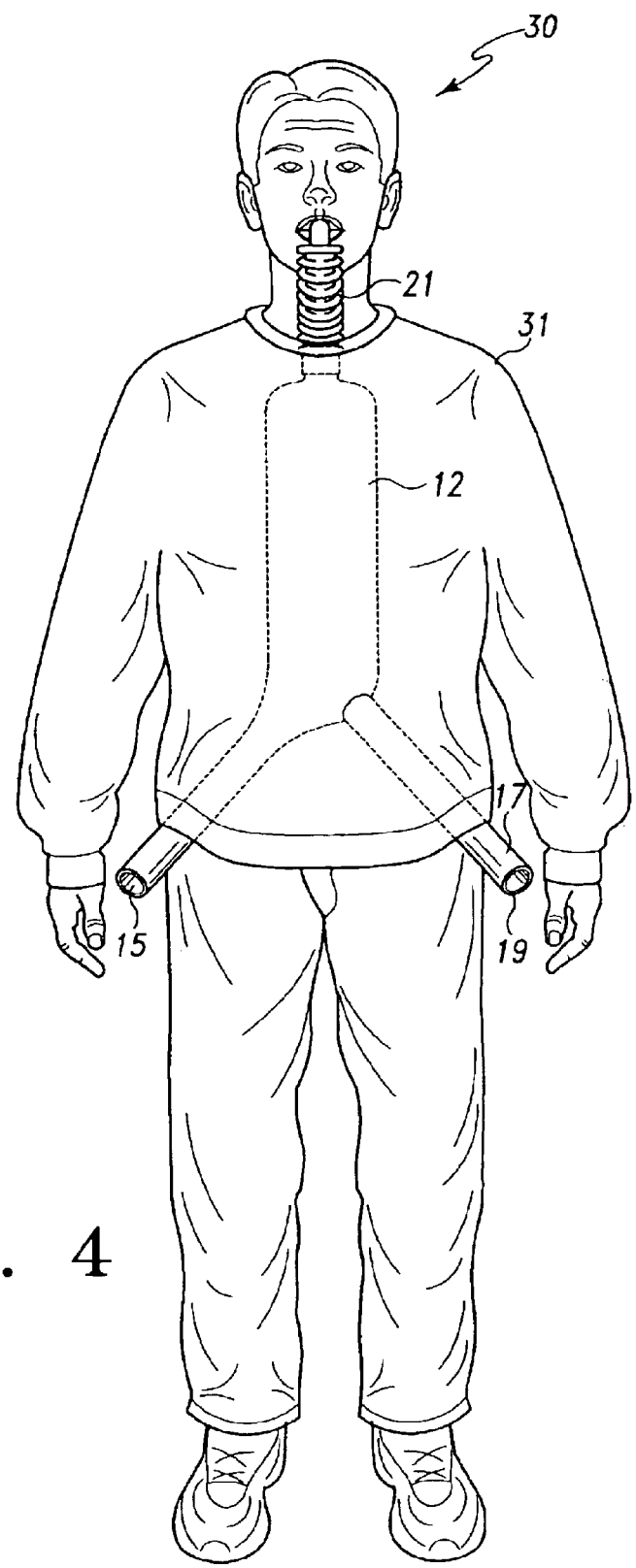
FIG. 4 is a front view of a person wearing a jacket and using the device shown in FIG. 1.

Referring now to FIG. 4, therein is shown a person 30 using the device 10 shown in FIG. 1 under a jacket 31 with the body 12 of the device 10 being positioned adjacent the chest of the user. It should be understood that the term "chest" is intended to include the abdomen of the user. The body 12 can be simply held in place under the jacket 31 or preferably, the body 12 is attached to the jacket 31. Alternatively, the body 12 can be carried by the user by the use of suspender straps, not shown, worn under the jacket 31. It should be understood that the opening 15 can be positioned as shown in FIG. 4, or to the front or rear of the person 30, or the opening 15 can be positioned under the clothing of the person 30 if desired. Similarly, the end 19 of the heat exchange conduit 17 can be positioned as shown in FIG. 4, or to the front or rear of the person 30, or the end 19 can be positioned under the clothing of the person 30 if desired. In addition, it may be desirable in some circumstances to place a knitted yarn tube around the heat exchange conduit 17 between the end 19 and the aperture 16 to thermally insulate this end of the heat exchange conduit 17.

Figure 5:
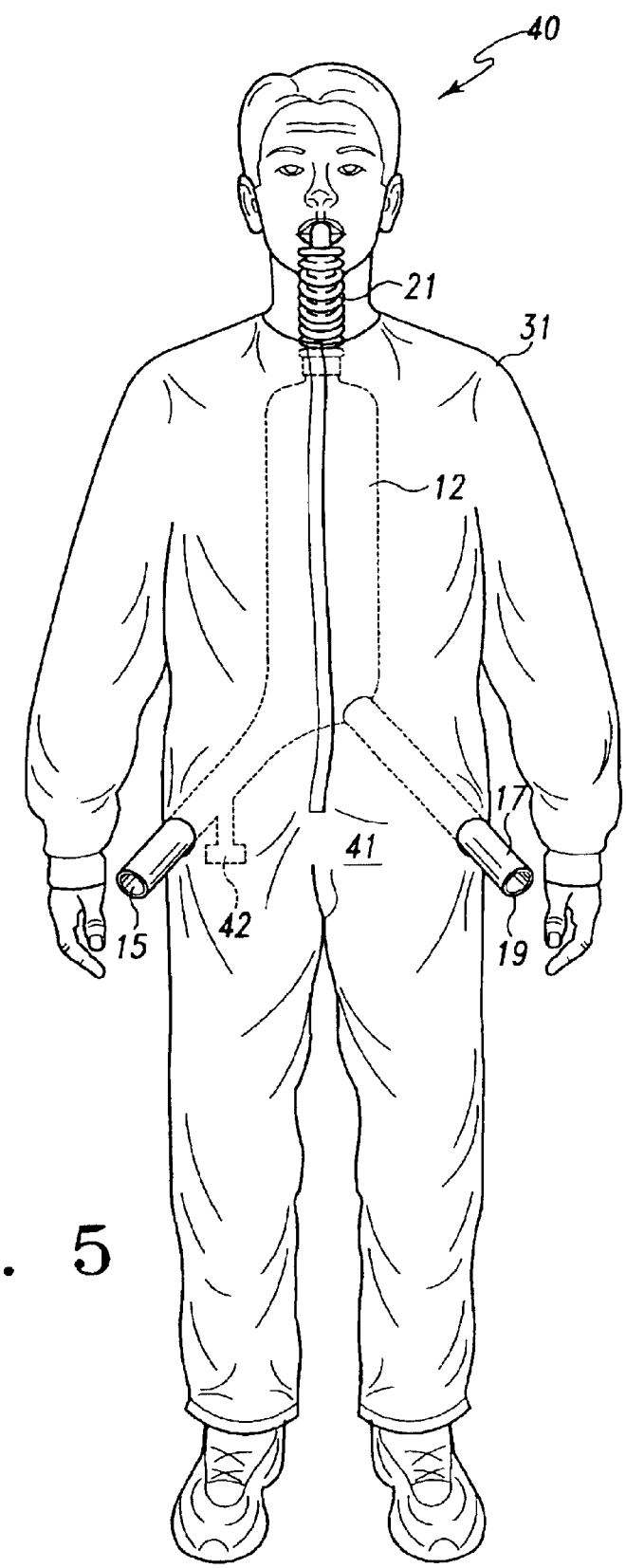
FIG. 5 is a front view of a person wearing a cold weather jump suit incorporating the device shown in FIG. 1.

Referring now to FIG. 5, therein is shown a person 40 using the device 10 shown in FIG. 1 that has been incorporated into a cold weather jump suit 41. The embodiment shown in FIG. 5 is highly preferred for use by persons who need to work in extremely cold conditions. Condensation and ice formation can be a problem at the opening 15 in extremely cold conditions. A condensation trap 42 incorporated into the body 12 may be helpful in collecting a portion of such condensation. A dust and/or toxic gas filter, not shown, can be attached to the end 19 of the heat exchange conduit 17 to help protect the user of the device 10 from dust and/or toxic gases or vapors. Again, it should be understood that the opening 15 can be incorporated as shown in FIG. 5, or to the front or rear of the person 40, or the opening 15 can be positioned under the jump suit of the person 40 if desired. Similarly, the end 19 of the heat exchange conduit 17 can be incorporated as shown in FIG. 5, or to the front or rear of the person 40, or the end 19 can be positioned under the jump suit of the person 40 if desired. In addition, it may be desirable in some circumstances to place a knitted yarn tube around the heat exchange conduit 17 between the end 19 and the aperture 16 to thermally insulate this end of the heat exchange conduit 17.

In its various embodiments, the device and method of the instant invention can be used by dog sledders, snowmobliers, ice skaters, skiers, firemen, policemen, soldiers, sailors, marines, construction workers, loggers, oil drillers, ice fishermen, commercial fishermen, road workers, mailmen, hunters, infirm persons sensitive to the cold and, in general, any person who works, plays or otherwise needs to breath more comfortably in a cold weather environment.

In conclusion, it is readily apparent that although the invention has been described in relation with its preferred embodiments, it should be understood that the instant invention is not limited thereby but is intended to cover all alternatives, modifications and equivalents that are included within the scope of the invention as defined by the following claims.

What is claimed is:

1. A breathing device, comprising: (a) a mouthpiece to be held in the mouth of a user of the device; (b) a hollow body defined by the walls of the body, the body having a mouth thereinto, the body having an opening therefrom, the body being perforated with an aperture; (c) a heat exchange conduit having a first end and a second end, the first end of the heat exchange conduit being positioned within the hollow body by way of the aperture, the second end of the heat exchange conduit being positioned outside of the wall of the hollow body, the wall of the hollow body being sealed to the heat exchange conduit at the aperture of the body; and (d) a flexible conduit having a first end and a second end, the first end of the flexible conduit being connected to the mouthpiece, the second end of the flexible conduit being connected to the mouth of the hollow body so that air breathed out of the lungs of a user through the mouthpiece flows through the flexible conduit, into the hollow body and then out the opening therefrom thereby heating the portion of the heat exchange conduit positioned within the hollow body and so that air then breathed into the second end of the heat exchange conduit flows into the hollow body heated by the heated portion of the heat exchange conduit positioned within the hollow body and then flows through the flexible conduit, through the mouthpiece and into the lungs of the user.

2. The breathing device of claim 1, further comprising a first check valve positioned in and sealed to the heat exchange conduit and a second check valve positioned in and sealed to the walls of the body adjacent the opening therefrom to prevent back flow of air through the heat exchange conduit when the user exhales through the device and to prevent backflow of air through the opening of the body when the user inhales air through the device, respectively.

3. The breathing device of claim 1, further comprising thermal insulation positioned on and around the flexible conduit.

4. The breathing device of claim 2, further comprising thermal insulation positioned on and around the flexible conduit.

5. The breathing device of claim 1, further comprising an article of cold weather outer clothing selected from the group consisting of a jacket, a coat and a jump suit, the body of the device being attached to the cold weather outer clothing so that the body of the device is positioned adjacent the chest of the user under the cold weather outer clothing when worn by the user.

6. The breathing device of claim 2, further comprising an article of cold weather outer clothing selected from the group consisting of a jacket, a coat and a jump suit, the body of the device being attached to the cold weather outer clothing so that the body of the device is positioned adjacent the chest of the user under the cold weather outer clothing when worn by the user.

7. The breathing device of claim 3, further comprising an article of cold weather outer clothing selected from the group consisting of a jacket, a coat and a jump suit, the body of the device being attached to the cold weather outer clothing so that the body of the device is positioned adjacent the chest of the user under the cold weather outer clothing when worn by the user.

8. The breathing device of claim 4, further comprising an article of cold weather outer clothing selected from the group consisting of a jacket, a coat and a jump suit, the body of the device being attached to the cold weather outer clothing so that the body of the device is positioned adjacent the chest of the user under the cold weather outer clothing when worn by the user.

9. A method for breathing more comfortably in cold weather by a person, comprising the steps of: (a) exhaling air warmed by the lungs of the person into contact with a heat exchange medium to heat the heat exchange medium, the heat exchange medium being positioned adjacent the chest of the person and under cold weather outer clothing worn by the person; and (b) inhaling air from contact with the heat exchange medium so that the inhaled air is heated by the heat exchange medium.

10. The method of claim 9, wherein the heat exchange medium is contained within a hollow body positioned adjacent the chest of the person and under cold weather outer clothing worn by the person.

11. The method of claim 9, wherein at least one half of the heat of the exhaled air is transferred to the heat exchange medium in step (a).

12. The method of claim 10, wherein at least one half of the heat of the exhaled air is transferred to the heat exchange medium in step (a).

\* \* \* \* \*